United States Patent [19]  
Cousse et al.

[11] Patent Number: 4,567,288  
[45] Date of Patent: * Jan. 28, 1986

[54] 1-ARYL 2-AMINOMETHYL CYCLOPROPANE CARBOXYLATES (Z)

[75] Inventors: Henri Cousse; Gilbert Mouzin; Bernard Bonnaud; Marie Charveron, all of Castres; Francois Fauran, Castanet-Tolosan, all of France

[73] Assignee: Pierre Fabre S.A., Castres, France

[ * ] Notice: The portion of the term of this patent subsequent to Mar. 26, 2002 has been disclaimed.

[21] Appl. No.: 656,443

[22] Filed: Oct. 1, 1984

Related U.S. Application Data

[63] Continuation of Ser. No. 390,811, Jun. 22, 1982, Pat. No. 4,507,318.

[30] Foreign Application Priority Data

Jun. 23, 1981 [FR] France ................................ 81 12311

[51] Int. Cl.[4] .................... C07C 79/46; C07C 101/30; C07C 101/02
[52] U.S. Cl. ......................................... 560/37; 560/21; 560/42; 560/48
[58] Field of Search ....................... 560/43, 37, 48, 21, 560/42

[56] References Cited

U.S. PATENT DOCUMENTS 4,507,318 3/1985 Cousse et al. .

OTHER PUBLICATIONS

Casadio et al., Boll. Chim. Farm. (1978) vol. 117, 331-342.

Primary Examiner—Bernard Helfin  
Attorney, Agent, or Firm—Gordon W. Hueschen

[57] ABSTRACT

The present invention concerns new derivatives of 1-aryl 2-aminomethyl cyclopropane carboxylates (Z), their preparation and their use as useful drugs for the treatment of various pains.

The new derivatives of the present invention have the general formula I

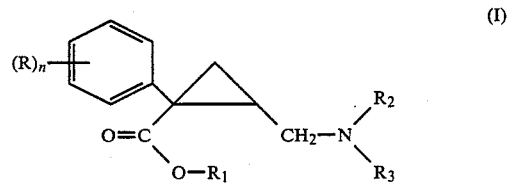

in which:

R represents a hydrogen or halogen atom, a $C_1$ to $C_4$ lower alkyl group, a $C_1$ to $C_4$ lower alkoxy group, or a nitro, amino, sulfamoyl or hydroxy group;

n represents the values 1, 2 or 3;

$(R)_n$ may together with the benzene ring also form the naphthyl group;

$R_1$ represents a linear or branched $C_1$ to $C_5$ alkyl or alkenyl group or an aryl or benzyl group;

$R_2$ and $R_3$ represent a hydrogen atom, a linear or branched $C_1$ to $C_5$ alkyl, alkenyl, alkynyl, hydroxyalkyl, alkoxyalkyl, carboxyalkyl or dialkylaminoalkyl group or an aryl, arylalkyl or cycloalkyl group;

$R_2$ and $R_3$ possibly also forming a heterocycle of 5 or 6 members with the adjacent nitrogen atom, provided however that when $R_1$ represents the ethyl radical and R represents a hydrogen atom, $R_2$ and $R_3$ cannot simultaneously represent a methyl radical.

8 Claims, No Drawings

1-ARYL 2-AMINOMETHYL CYCLOPROPANE CARBOXYLATES (Z)

This is a continuation of application Ser. No. 390,811, filed June 22, 1982, now U.S. Pat. No. 4,507,318, issued Mar. 26, 1985.

The present invention, made at the Pierre FABRE Research Center, concerns new derivatives of 1-aryl 2-aminomethyl cyclopropane carboxylic esters (Z), their method of preparation and their use in therapy and in particular in the treatment of various pains.

The closest known prior art can be illustrated, for instance, by French Pat. No. 75 07120 which covers a method of preparing 1-aryl 2-hydroxymethyl cyclopropane carboxylic acids.

These acid-alcohol derivatives have furthermore been the subject matter of an article by G. MOUZIN, H. COUSSE and B. BONNAUD in "Synthesis 1978, 304," reprinted in "Synthetic Methods of Organic Chemistry" (Editor W. THEILHEIMER) 34, 1980, 317. The pharmacological study of the derivatives of 1-phenyl-2-hydroxymethyl cyclopropane carboxylic acid described by S. CASADIO, B. BONNAUD, G. MOUZIN and H. COUSSE in Boll. Chim. Farm. 117, 1978, 331, has shown the slight pharmacological activity of these derivatives.

The present invention relates to new compounds, which differ from those of the prior art indicated above; they are amino cyclopropane ester derivatives of the formula:

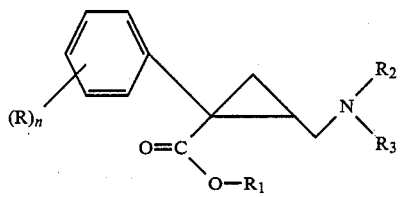

Now it has been shown that the modulations effected at the level of the functional groups borne by the cyclopropane group confer very interesting pharmacological properties to these new amino cyclopropane esters and more particularly an analgesic action which makes it possible to use these compounds for the treatment of various pains.

The present invention concerns new 1-aryl 2-aminomethyl cyclopropane carboxylate derivatives (Z) of general formula I:

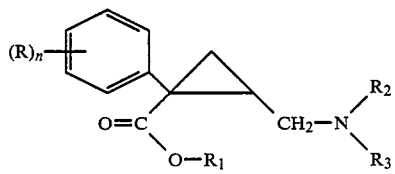

in which:

R represents a hydrogen or halogen atom, a lower alkyl group of $C_1$ to $C_4$, lower alkoxy of $C_1$ to $C_4$, hydroxy, nitro, amino or sulfamoyl;

n represents 1, 2 or 3;

$(R)_n$ may also, together with the benzene cycle, form the naphthyl group;

$R_1$ represents a $C_1$ to $C_5$ linear or branched alkenyl or alkyl group or an aryl or benzyl group;

$R_2$ and $R_3$ represent a hydrogen atom, a $C_1$ to $C_5$ linear or branched alkyl, alkenyl, alkynyl, hydroxyalkyl, carboxyalkyl, alkoxyalkyl or dialkylaminoalkyl group, or an aryl, arylalkyl or cycloalkyl group;

$R_2$ and $R_3$ possibly also forming with the neighboring nitrogen atom a heterocycle having 5 or 6 members, provided however that when $R_1$ represents the ethyl radical and R represents a hydrogen atom, $R_2$ and $R_3$ cannot simultaneously represent a methyl radical. All numbers of carbon atoms given are inclusive of the largest number stated.

The heterocycle formed by the radicals $R_2$ and $R_3$ with the neighboring nitrogen atom designates more particularly a heterocycle of a non-aromatic character with five or six members which may possibly contain one or more other heteroatoms selected primarily from among nitrogen and oxygen and being possibly furthermore substituted, for instance in para position of the said adjacent nitrogen atom or on the second heteroatom, by an aryl radical, particularly a phenyl radical which in its turn is substituted by one or more other halogen atoms, such as chlorine.

The present invention also relates to salts of compounds of general formula I with therapeutically acceptable inorganic or organic acids. By way of illustration and not of limitation of these salts, mention may be made of the hydrohalides such as hydrochloride, fumarate, maleate, oxalate, citrate and glutamate.

The present invention also concerns a method of preparing compounds of general formula (I) consisting in treating the lactone of general formula (II) by an alcohol or a phenol in the presence of a thionyl halide. The lactone of the general formula (II) can for instance be obtained by the method of preparation described in the applicant's French Pat. No. 75 07120. The halogenated intermediary of general formula (III) is then condensed on an amine. The method of preparation is illustrated by the following reaction scheme:

Reaction Scheme

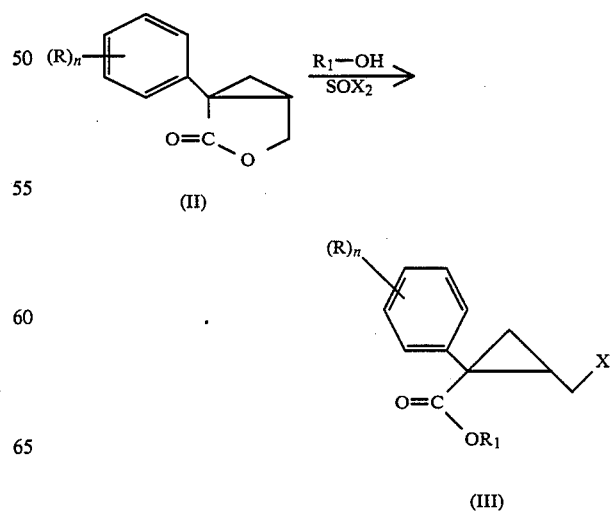

-continued
Reaction Scheme

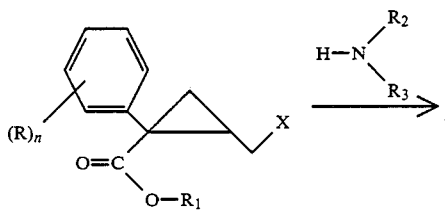

(III)

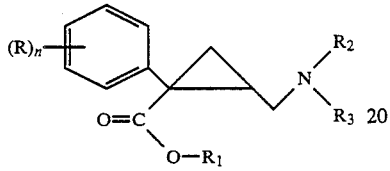

(I)

in which
X represents a halogen
R, $R_1$, $R_2$, $R_3$ and n have the meaning given previously in connection with general formula I.

The following examples illustrate the invention without, of course, limiting its scope. In the formulas of the compounds of the following examples the symbol Et designates the ethyl radical.

EXAMPLE 1

Preparation of the hydrochloride of 1-phenyl 1-ethoxycarbonyl 2-pyrrolidinomethyl cyclopropane (Z)

(a) Preparation of the 1-phenyl 1-ethoxycarbonyl 2-chloromethyl cyclopropane (Z)

126 cc (1.8 mole) of thionyl chloride are introduced with agitation over the course of 2½ hours into 500 cc of ethanol at −10° C. whereupon 100 g (0.57 mole) of 1-phenyl-2-oxo-3-oxa-bicyclo (3.1.0) hexane are added. The mixture is allowed to return to room temperature while agitated for 12 hours.

The reaction solvent is evaporated and rectified under reduced pressure.

A product of the formula

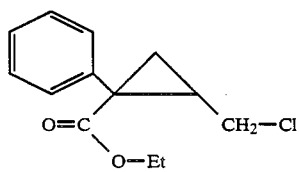

is recovered in a yield of 95%.
Empirical formula: $C_{13}H_{15}ClO_2$.
Molecular weight: 238.71.
Boiling point: 95°–98° C./0.04 mm Hg.
Melting point: 45°–45° C.

(b) 1-phenyl 1-ethoxycarbonyl 2-pyrrolidinomethyl cyclopropane hydrochloride (Z)

To a solution of (0.03 mole) of 1-phenyl 1-ethoxycarbonyl 2-chloromethyl cyclopropane (Z) in 60 cc of toluene there are added 6.4 g (0.09 mole) of pyrrolidine.

The reaction solution is maintained under reflux for five hours. The solvent is evaporated to dryness.

The residual mass is treated with a bicarbonate solution; it is extracted with ethyl ether and then washed with water and dried over sodium sulfate.

The free base is treated with an ethanol solution saturated with hydrochloric acid; upon the addition of ether the salt precipitates and the product of the formula

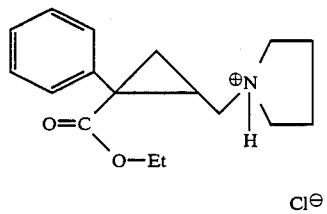

is recovered in a yield of 85%.
Empirical formula: $C_{17}H_{24}ClNO_2$.
Molecular weight: 309.8.
Crystals: white.
Melting point: 140° C.
Plate chromatography:
support: silical gel 60 F 254 Merck
solvent: butanol/acetic acid/water 6/2/2
development: UV and iodine
Rf: 0.49
Solubility: 50% soluble in water.

EXAMPLE 2

Hydrochloride of 1-phenyl 1-ethoxycarbonyl 2-(2-phenyl ethyl) amino-methyl cyclopropane (Z)

In a manner similar to that described in Example 1b, but using 2-phenyl ethylamine, there is obtained the product of the formula:

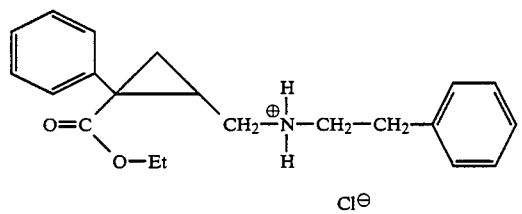

Empirical formula: $C_{21}H_{26}ClNO_2$.
Molecular weight: 359.9.
Crystals: white.
Melting point: 156° C.
Plate chromatography:
support: silica gel 60 F 254 Merck
solvent: chloroform-methanol
development: UV and iodine
Rf: 0.62
Solubility: 50% soluble in water.

EXAMPLE 3

Hydrochloride of 1-phenyl 1-ethoxycarbonyl 2-methyl amino-methyl cyclopropane (Z)

In a manner similar to that described in Example 1b, but using methylamine, the product of the formula:

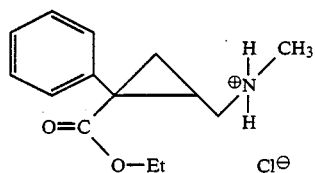

is obtained.
  Empirical formula: $C_{14}H_{20}ClNO_2$.
  Molecular weight: 269.8.
  Crystals: white.
  Melting point: 132° C.
  Plate chromatography:
  support: silica gel 60 F 254 Merck
  solvent: butanol/acetic acid/water 6/2/2
  development: UV and iodine
  Rf: 0.54
  Solubility: 50% soluble in water.

EXAMPLE 4

Hydrochloride of 1-phenyl 1-ethoxycarbonyl 2-diethyl amino-methyl cyclopropane (Z)

In a manner similar to that described in Example 1b, but using diethylamine a product of the formula

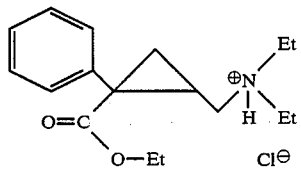

is obtained.
  Empirical formula: $C_{17}H_{26}ClNO_2$.
  Molecular weight: 311.86.
  Crystals: white.
  Melting point: 132° C.
  Plate chromatography:
  support: silica gel 60 F 254 Merck
  solvent: butanol/acetic acid/water 6/2/2
  development: UV and iodine
  Rf: 0.44
  Solubility: 50% soluble in water.

EXAMPLE 5

Hydrochloride of 1-phenyl 1-ethoxycarbonyl 2-(benzyl methyl amino methyl) cyclopropane (Z)

In a manner similar to that described in Example 1b, but using N-methyl benzylamine, the product of the formula

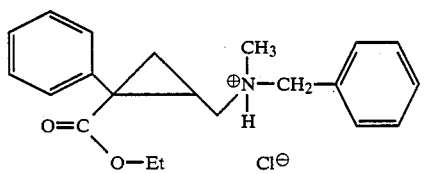

is obtained.
  Empirical formula: $C_{21}H_{26}ClNO_2$.
  Molecular weight: 359.9.
  Crystals: white.
  Melting point: 130° C.
  Plate chromatography:
  support: silica gel 60 F 254 Merck
  solvent: butanol/acetic acid/water 6/2/2
  development: UV and iodine
  Rf: 0.6
  Solubility: 10% soluble in water.

EXAMPLE 6

Hydrochloride of 1-phenyl 1-ethoxycarbonyl-2-terbutylamino-methyl cyclopropane (Z)

In a manner similar to that described in Example 1b, but using terbutylamine, there is obtained the product of the formula:

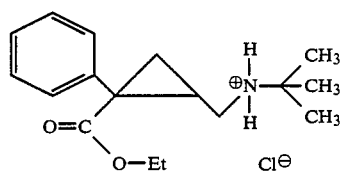

Empirical formula: $C_{17}H_{26}ClNO_2$.
  Molecular weight: 311.85.
  Crystals: white.
  Melting point: 155° C.
  Plate chromatography:
  support: silica gel 60 F 254 Merck
  solvent: butanol/acetic acid/water 6/2/2
  development: UV and iodine
  Rf: 0.59
  Solubility: 17% soluble in water.

EXAMPLE 7

Maleate of 1-phenyl 1-ethoxycarbonyl 2-di(2'-hydroxyethyl)amino-methyl cyclopropane (Z)

In a manner similar to that described in Example 1b, but using diethanolamine and maleic acid as salifying agent, there is obtained a product of the formula:

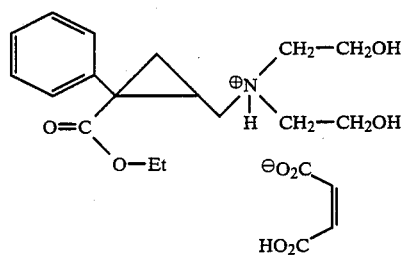

Empirical formula: $C_{21}H_{29}NO_8$.
  Molecular weight: 423.4.
  Crystals: white.
  Melting point: 102° C.
  Plate chromatography:
  support: silica gel 60 F 254 Merck
  solvent: butanol/acetic acid/water 6/2/2
  development UV and iodine
  Rf: 0.47
  Solubility: 50% soluble in water.

EXAMPLE 8

Dihydrochloride of 1-phenyl 1-ethoxycarbonyl 2-(4'-phenyl-piperazino methyl)cyclopropane (Z)

In a manner similar to that described in Example 1b, but using N-phenyl piperazine, there is obtained a product of the formula:

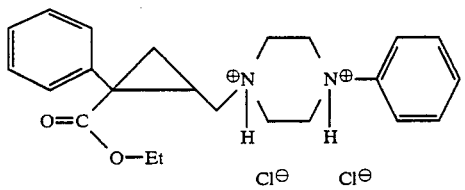

Empirical formula: $C_{23}H_{30}Cl_2N_2O_2$.
Molecular weight: 437.4.
Crystals: white.
Melting point: 202° C.
Plate chromatography:
support: silica gel 60 F 254 Merck
solvent: butanol/acetic acid/water 6/2/2/
development: UV and iodine
Rf: 0.72
Solubility: 0.5% soluble in water.

EXAMPLE 9

Hydrochloride of 1-phenyl 1-ethoxycarbonyl-2-morpholino methyl cyclopropane (Z)

In a manner similar to that described in Example 1b but using morpholine, there is obtained a product of the formula:

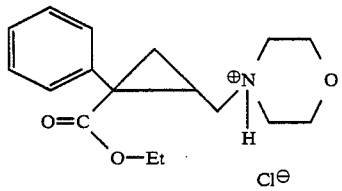

Empirical formula: $C_{17}H_{24}ClNO_3$.
Molecular weight: 325.8.
Crystals: white.
Melting point: 195° C.
Plate chromatography:
support: silica gel 60 F 254 Merck
solvent: butanol/acetic acid/water 6/2/2
development: UV and iodine
Rf: 0.52
Solubility: 50% soluble in water.

EXAMPLE 10

Fumarate of 1-phenyl 1-ethoxycarbony 2-N-(2'-hydroxyethyl)N-methyl amino-methyl cyclopropane (Z)

In a manner similar to that described in Example 1b but using N-methyl ethanolamine and fumaric acid as salifying agent, there is obtained a product of the formula:

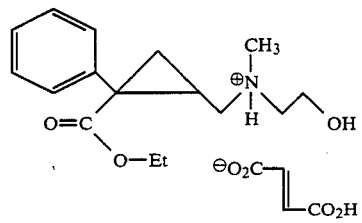

Empirical formula: $C_{20}H_{27}NO_7$.
Molecular weight: 393.42.
Crystals: white.
Melting point: 139° C.
Plate chromatography:
support: silica gel 60 F 254 Merck
solvent: butanol/acetic acid/water 6/2/2
development: UV and iodine
Rf: 0.4
Solubility: 8% soluble in water.

EXAMPLE 11

Hydrochloride of 1-phenyl 1-ethoxycarbonyl 2-dibenzyl amino-methyl cyclopropane (Z)

In a manner similar to that described in Example 1b, but using dibenzylamine, there is obtained a product of the formula:

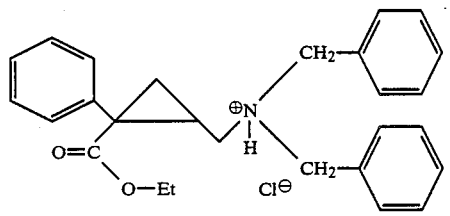

Empirical formula: $C_{27}H_{30}ClNO_2$.
Molecular weight: 436.
Crystals: white.
Melting point: 185° C.
Plate chromatography:
support: silica gel 60 F 254 Merck
solvent: butanol/acetic acid/water 6/2/2
development: UV and iodine
Rf: 0.77
Solubility: insoluble in water, 2% soluble in DMA.

EXAMPLE 12

Hydrochloride of 1-phenyl 1-ethoxycarbonyl-2-(1'-1'-dimethyl-2'-propynyl amino methyl)cyclopropane (Z)

In a manner similar to that described in Example 1b, but using 2-amino-2-methyl-3-butyne, there is obtained a product of the formula:

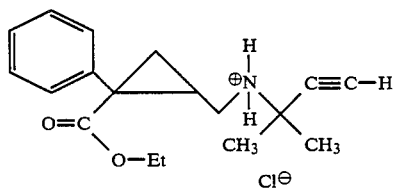

Empirical formula: $C_{18}H_{24}ClNO_2$.
Molecular weight: 321.8.
Crystals: white.
Melting point: 194° C.
Plate chromatography:
support: silica gel 60 F 254 Merck
solvent: butanol/acetic acid/water 6/2/2
development: UV and iodine
Rf: 0.65
Solubility: 3% soluble in water.

EXAMPLE 13

Hydrochloride of 1-phenyl 1-ethoxycarbonyl 2-(2'-ethoxy ethylaminomethyl)cyclopropane (Z)

In a manner similar to that described in Example 1b, but using 2-ethoxy ethylamine, there is obtained a product of the formula:

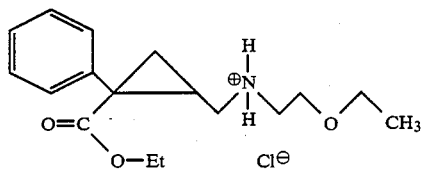

Empirical formula: $C_{17}H_{26}ClNO_3$.
Molecular weight: 327.8.
Crystals: white.
Melting point: 100° C.
Plate chromatography:
support: silica gel 60 F 254 Merck
solvent: butanol/acetic acid/water 6/2/2
development: UV and iodine
Rf: 0.59
Solubility: 50% soluble in water.

EXAMPLE 14

Hydrochloride of 1-phenyl-1-ethoxycarbonyl 2-benzyl amino methyl cyclopropane (Z)

In a manner similar to that described in Example 1b, but using benzylamine, there is obtained a product of the formula:

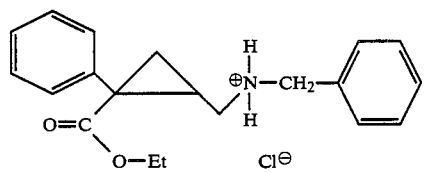

Empirical formula: $C_{20}H_{24}ClNO_2$.
Molecular weight: 345.9.
Crystals: white.
Melting point: 180° C.
Plate chromatography:
support: silica gel 60 F 254 Merck
solvent: butanol/acetic acid/water 6/2/2
development: UV and iodine
Rf: 0.65
Solubility: 1% soluble in water.

EXAMPLE 15

Hydrochloride of 1-phenyl 1-ethoxycarbonyl 2-isopropyl aminomethyl cyclopropane (Z)

In a manner similar to that described in Example 1b, but using isopropylamine, there is obtained a product of the formula:

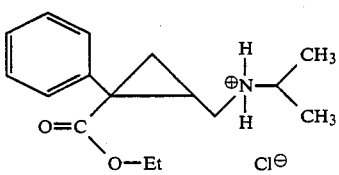

Empirical formula: $C_{16}H_{24}ClNO_2$.
Molecular weight: 297.8.
Crystals: white.
Melting point: 131° C.
Plate chromatography:
support: silica gel 60 F 254 Merck
solvent: butanol/acetic acid/water 6/2/2
development: UV and iodine
Rf: 0.52
Solubility: 50% soluble in water.

EXAMPLE 16

Maleate of 1-phenyl 1-ethoxycarbonyl 2-diisopropyl aminomethyl cyclopropane (Z)

In a manner similar to that described in Example 1b, but using diisopropylamine and maleic acid as salifying agent, there is obtained a product of the formula:

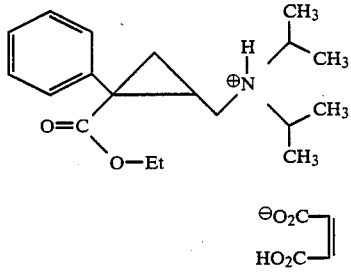

Empirical formula: $C_{23}H_{33}NO_6$.
Molecular weight: 419.5.
Crystals: white.
Melting point: 108° C.
Plate chromatography:
support: silica gel 60 F 254 Merck
solvent: butanol/acetic acid/water 6/2/2
development: UV and iodine
Rf: 0.5
Solubility: 10% soluble in water.

EXAMPLE 17

Fumarate of 1-phenyl 1-ethoxycarbonyl 2-(N-methyl-N-ethyl-amino)methyl cyclopropane (Z)

In a manner similar to that described in Example 1b, but using N-methyl-N-ethylamine, and fumaric acid as salifying agent, there is obtained a product of the formula:

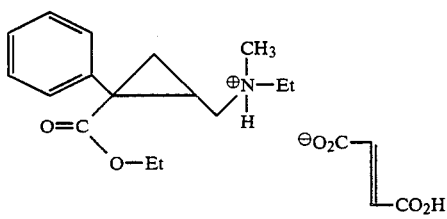

Empirical formula: $C_{20}H_{27}NO_6$.
Molecular weight: 377.4.
Crystals: white.
Melting point: 98° C.
Plate chromatography:
support: silica gel 60 F 254 Merck
solvent: butanol/acetic acid/water 6/2/2
development: UV and iodine
Rf: 0.45
Solubility: 50% soluble in water.

EXAMPLE 18

Fumarate of 1-phenyl 1-ethoxycarbonyl 2-(N-methyl-N-pentylamino)methyl cyclopropane (Z)

In a manner similar to that described in Example 1b, but using N-methyl pentylamine and fumaric acid as salifying agent, there is obtained a product of the formula:

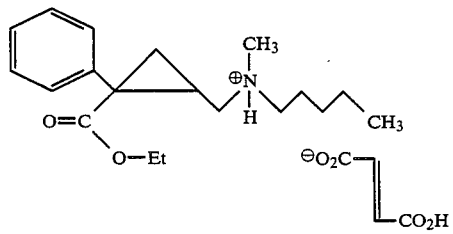

Empirical formula: $C_{23}H_{33}NO_6$.
Molecular weight: 419.5.
Crystals: white.
Melting point: 100° C.
Plate chromatography:
support: silica gel 60 F 254 Merck
solvent: butanol/acetic acid/water 6/2/2
development: UV and iodine
Rf: 0.61
Solubility: 3% soluble in water.

EXAMPLE 19

Fumarate of 1-phenyl 1-ethoxycarbonyl 2-N-methyl-N-cyclohexyl-aminomethyl cyclopropane (Z)

In a manner similar to that described in Example 1b, but using N-methyl cyclohexylamine and fumaric acid as salifying agent, there is obtained a product of the formula:

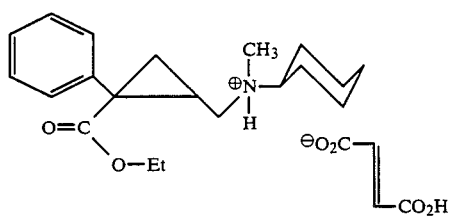

Empirical formula: $C_{24}H_{33}NO_6$.
Molecular weight: 431.5.
Crystals: white.
Melting point: 179° C.
Plate chromatography:
support: silica gel 60 F 254 Merck
solvent: butanol/acetic acid/water 6/2/2
development: UV and iodine
Rf: 0.56
Solubility: insoluble in water, 5% soluble in DMA.

EXAMPLE 20

Hydrochloride of 1-phenyl 1-ethoxycarbonyl 2-(4'-phenyl piperidino)methyl cyclopropane (Z)

In a manner similar to that described in Example 1b, but using 4-phenyl piperidine, there is obtained a product of the formula:

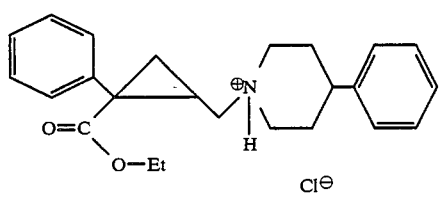

Empirical formula: $C_{24}H_{30}ClNO_2$.
Molecular weight: 399.9.
Crystals: white.
Melting point: 165° C.
Plate chromatography:
support: silica gel 60 F 254 Merck
solvent: butanol/acetic acid/water 6/2/2
development: UV and iodine
Rf: 0.71
Solubility: insoluble in water, 50% soluble in DMA.

EXAMPLE 21

Dihydrochloride of 1-phenyl 1-ethoxycarbonyl-2-(N-methyl N-(2'-dimethylamino)ethyl)aminomethyl cyclopropane (Z)

In a manner similar to that described in Example 1b, but using N,N,N'-trimethyl ethylene diamine, there is obtained a product of the formula:

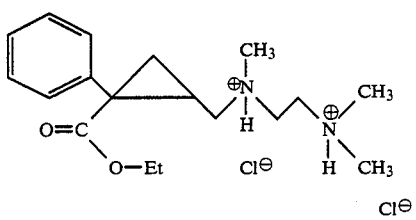

Empirical formula: $C_{18}H_{30}Cl_2N_2O_2$.
Molecular weight: 377.3.
Crystals: white.
Melting point: 210° C.
Plate chromatography:
support: silica gel 60 F 254 Merck
solvent: chloroform/methanol/ammonia 80/18/2
development: UV and iodine
Rf: 0.55
Solubility: 50% soluble in water.

EXAMPLE 22

Hydrochloride of 1-phenyl 1-ethoxycarbonyl 2-cyclohexylaminomethyl cyclopropane (Z)

In a manner similar to that described in Example 1b, but using cyclohexylamine, there is obtained a product of the formula:

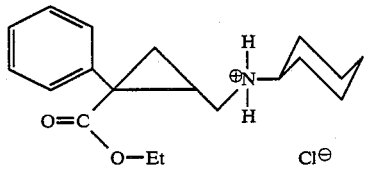

Empirical formula: $C_{19}H_{28}ClNO_2$.
Molecular weight: 377.9.
Crystals: white.
Melting point: 152° C.
Plate chromatography:
support: silica gel 60 F 254 Merck
solvent: chloroform/methanol 85/15
development: UV and iodine
Rf: 0.45

EXAMPLE 23

Hydrochloride of 1-phenyl 1-ethoxycarbonyl 2-piperidino methyl cyclopropane (Z)

In a manner similar to that described in Example 1b, but using piperidine, there is obtained a product of the formula:

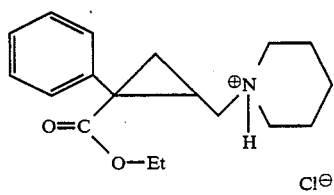

Empirical formula: $C_{18}H_{26}ClNO_2$.
Molecular weight: 323.8.
Crystals: white.
Melting point: 175° C.

Plate chromatography:
support: silica gel 60 F 254 Merck
solvent: chloroform/methanol 85/15
development: UV and iodine
Rf: 0.59

EXAMPLE 24

Hydrochloride of 1-phenyl 1-ethoxycarbonyl 2-N-methyl N-phenyl aminomethyl cyclopropane (Z)

In a manner similar to that described in FIG. 1b, but using N-methyl aniline, there is obtained a product of the formula:

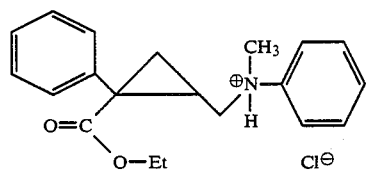

Empirical formula: $C_{20}H_{24}ClNO_2$.
Molecular weight: 345.8.
Crystals: white.
Melting point: 120° C.
Plate chromatography:
support: silica gel 60 F 254 Merck
solvent: ether of ethyl petroleum acetate 90/10
development: UV and iodine
Rf: 0.3.

EXAMPLE 25

Dihydrochloride of 1-phenyl 1-ethoxycarbonyl 2-[4'-(metachlorophenyl)piperazino]methyl cyclopropane (Z)

In a manner similar to that described in Example 1b, but using 4-metachlorophenyl piperazine, there is obtained a product of the formula:

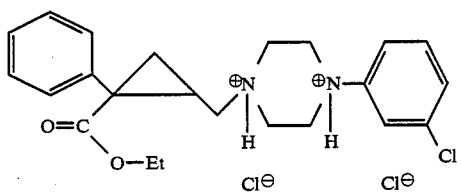

Empirical formula: $C_{23}H_{29}Cl_3N_2O_2$.
Molecular weight: 471.8.
Crystals: white.
Melting point: 185° C.
Plate chromatography:
support: silica gel 60 F 254 Merck
solvent: butanol/acetic acid/water 6/2/2
development: UV and iodine
Rf: 0.71

EXAMPLE 26

Oxalate of 1-phenyl 1-ethoxycarbonyl 2-N-methyl-N-allyl aminomethyl cyclopropane (Z)

In a manner similar to that described in Example 1b, but using N-methyl allylamine and oxalic acid as salifying agent, there is obtained a product of the formula:

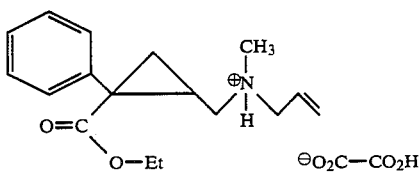

Empirical formula: $C_{19}H_{25}NO_6$.
Molecular weight: 327.4.
Crystals: white.
Melting point: 128° C.
Plate chromatography:
support: silica gel 60 F 254 Merck
solvent: butanol/acetic acid/water 6/2/2
development: UV and iodine
Rf: 0.5

EXAMPLE 27

1-phenyl 1-ethoxycarbonyl 2-N-ethyl-N-(2-ethoxyethyl)aminomethyl cyclopropane (Z)

In a manner similar to that described in Example 1b, but using N-ethyl-2-ethoxy ethylamine, there is obtained a product of the formula

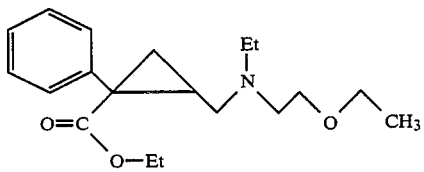

Empirical formula: $C_{19}H_{29}NO_3$.
Molecular weight: 319.2.
Boiling point: 120° C./$10^{-2}$ mmHg.
Plate chromatography:
support: silica gel 60 F 254 Merck
solvent: ethyl acetate/petroleum ether 50/50
development: UV and iodine
Rf: 0.3

EXAMPLE 28

Hydrochloride of 1-phenyl 1-ethoxycarbonyl 2-[(2-methyl N-p-hydroxyphenyl ethyl)-aminomethyl]cyclopropane (Z)

In a manner similar to that described in Example 1b, but using N-methyl tyramine, there is obtained a product of the formula:

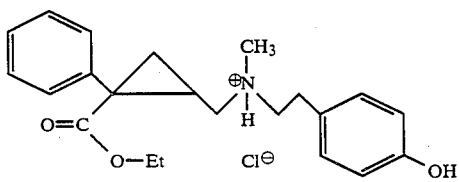

Empirical formula: $C_{22}H_{28}ClNO_3$.
Molecular weight: 389.9.
Crystals: white.
Melting point: 157° C.
Plate chromatography:
support: silica gel 60 F 254 Merck
solvent: chloroform/methanol/ammonia
development: UV and iodine
Rf: 0.57

EXAMPLE 29

Maleate of 1-phenyl 1-ethoxycarbonyl 2-(N-methyl-N-ethoxy carbonyl)aminomethyl cyclopropane (Z)

In a manner similar to that described in Example 1b, but using methyl sarcosinate, there is obtained a product of the formula:

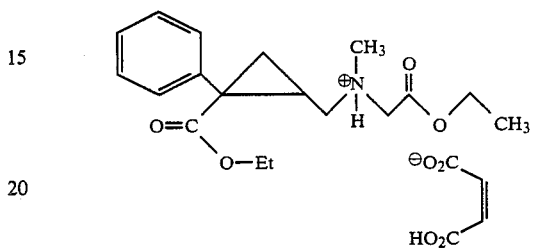

Empirical formula: $C_{22}H_{29}NO_8$.
Molecular weight: 435.46.
Crystals: white.
Melting point: 84° C.
Plate chromatography:
support: silica gel 60 F 254 Merck
solvent: petroleum ethyl ether acetate
development: UV and iodine
Rf: 0.49

EXAMPLE 30

Hydrochloride of 1-phenyl-1-ethoxycarbonyl 2[N-methyl-2-N-phenyl ethyl)-aminomethyl]cyclopropane (Z)

In a manner similar to that described in Example 1b, but using N-methyl phenyl ethylamine, there is obtained a product of the formula

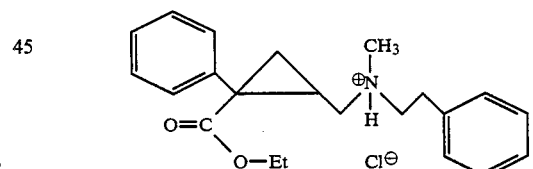

Empirical formula: $C_{22}H_{28}ClNO_2$
Molecular weight: 373.9
Crystals: white
Melting point: 112° C.
Plate chromatography:
support: silica gel 60 F 254 Merck
solvent: butanol/acetic acid/water 6/2/2
development: UV and iodine
Rf: 0.66

EXAMPLE 31

Hydrochloride of 1-phenyl 1-ethoxycarbonyl 2-(1'-benzyl ethylamino methyl)-cyclopropane (Z)

In a manner similar to that described in Example 1b, but using DL amphetamine, there is obtained a product of the formula:

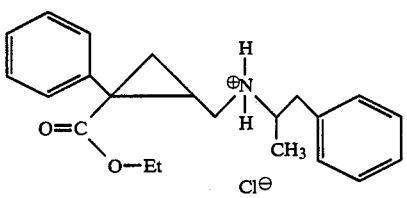

Empirical formula: $C_{22}H_{28}ClNO_2$.
Molecular weight: 373.9.
Crystals: white.
Melting point: 135° C.
Plate chromatography:
support: silica gel 60 F 254 Merck
solvent: chloroform/methanol 5/95
development: UV and iodine
Rf: 0.33

EXAMPLE 32

Hydrochloride of 1-phenyl 1-ethoxycarbonyl 2-(N-methyl-N-butyl aminomethyl)cyclopropane (Z)

In a manner similar to that described in Example 1b, but using N-methyl butylamine, there is obtained a product of the formula:

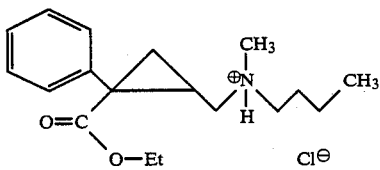

Empirical formula: $C_{18}H_{17}ClNO_2$.
Molecular weight: 325.9.
Crystals: white.
Melting point: 132° C.
Plate chromatography:
support: silica gel 60 F 254 Merck
solvent: butanol/acetic acid/water 6/2/2
development: UV and iodine
Rf: 0.59

EXAMPLE 33

1-phenyl-1-ethoxycarbonyl(N-methyl 2'-N-tetrahydrofurfuryl)-aminomethyl cyclopropane (Z)

In a manner similar to that described in Example 1b, but using N-methyl tetrahydrofurfurylamine, there is obtained a product of the formula:

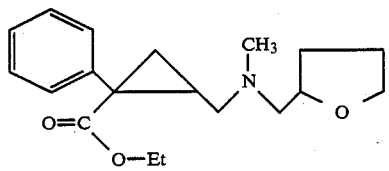

Empirical formula: $C_{19}H_{27}NO_3$.
Molecular weight: 317.4.
Oil.
Boiling point: 152° under a pressure of $10^{-1}$ mmHg
Plate chromatography:
support: silica gel 60 F 254 Merck
solvent: butanol/acetic acid/water 6/2/2
development: UV and iodine
Rf: 0.41

EXAMPLE 34

Hydrochloride of 1-phenyl 1-methoxycarbonyl 2-dimethyl-amino-methyl cyclopropane (Z)

In a manner similar to that described in Example 1a, but using methyl alcohol, and as in 1b using dimethylamine, there is obtained a product of the formula:

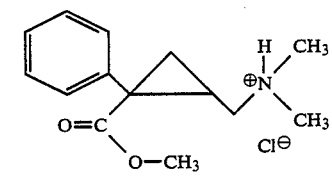

Empirical formula: $C_{14}H_{20}ClNO_2$.
Molecular weight: 269.7.
Crystals: white.
Melting point: 150° C.
Plate chromatography:
support: silica gel 60 F 254 Merck
solvent: butanol/acetic acid/water 6/2/2
revelation: UV and iodine
Solubility: 50% soluble in water.

EXAMPLE 35

Fumarate of 1-phenyl 1-propyloxycarbonyl 2-dimethyl aminomethyl cyclopropane (Z)

In a manner similar to that described in Example 1a, but using propyl alcohol and in 1b using dimethylamine and fumaric acid as salifying agent, there is obtained a product of the formula:

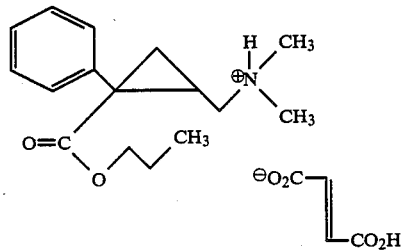

Empirical formula: $C_{20}H_{27}NO_6$.
Molecular weight: 377.4.
Crystals: white.
Melting point: 114° C.
Plate chromatography:
support: silica gel 60 F 254 Merck
solvent: chloroform/methanol/ammonia 80/18/2
development: UV and iodine
Rf: 0.76
Solubility: 15% soluble in water.

EXAMPLE 36

Hydrochloride of 1-phenyl 1-isopropyloxy carbonyl 2-dimethylamino methyl cyclopropane (Z)

In a manner similar to that described in Example 1a, but using isopropyl alcohol, and in 1b but using dimethylamine, there is obtained a product of the formula:

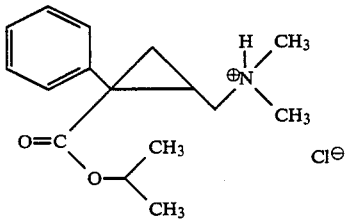

Empirical formula: $C_{16}H_{24}ClNO_2$.
Molecular weight: 297.8.
Crystals: white.
Melting point: 158° C.
Plate chromatography:
support: silica gel 60 F 254 Merck
solvent: butanol/acetic acid/water 6/2/2
development: UV and iodine
Rf: 0.41

EXAMPLE 37

Hydrochloride of 1-phenyl 1-benzyloxy carbonyl-2-dimethyl aminomethyl cyclopropane (Z)

In a manner similar to that described in Example 1a, but using benzyl alcohol, and in 1b but using dimethylamine, there is obtained a product of the formula:

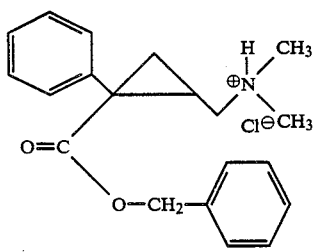

Empirical formula: $C_{20}H_{24}ClNO_2$
Molecular weight: 345.9
Melting point: 132° C.
Plate chromatography:
support: silica gel 60 F 254 Merck
solvent: butanol/acetic acid/water 6/2/2
development: UV and iodine
Rf: 0.52

EXAMPLE 38

Hydrochloride of 1-phenyl 1-phenoxycarbonyl 2-dimethyl amino methyl cyclopropane (Z)

In a manner similar to that described in Example 1a, but using phenol and in 1b but using dimethylamine, there is obtained a product of the formula:

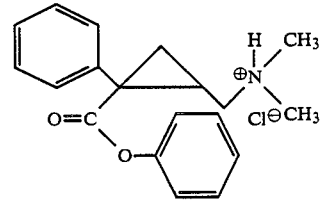

Empirical formula: $C_{19}H_{22}ClNO_2$.
Molecular weight: 315.8.
Crystals: white.
Melting point: 234° C.
Plate chromatography:
support: silica gel 60 F 254 Merck
solvent: butanol/acetic acid/water 6/2/2
development: UV and iodine
Rf: 0.42

EXAMPLE 39

Fumarate of 1-phenyl 1-allyloxycarbonyl 2-dimethylaminomethyl cyclopropane (Z)

In a manner similar to that described in Examples 1a and 1b, but using allyl alcohol and dimethylamine, there is obtained a product of the formula:

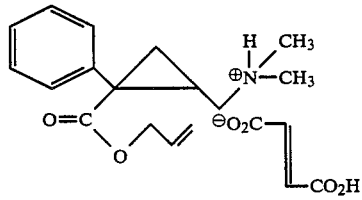

Empirical formula: $C_{20}H_{25}NO_6$.
Molecular weight: 375.4.
Crystals: white.
Melting point: 92° C.
Plate chromatography:
support: silica gel 60 F 254 Merck
solvent: butanol/acetic acid/water 6/2/2
development: UV and iodine
Rf: 0.4

EXAMPLE 40

Fumarate of 1-phenyl 1-(3'-methyl-2-butenyloxy carbonyl)-2-dimethylaminomethyl cyclopropane In a manner similar to that described in Examples 1a and 1b, but using 3-methyl-2-butene-1-ol and dimethylamine, there is obtained a product of the formula:

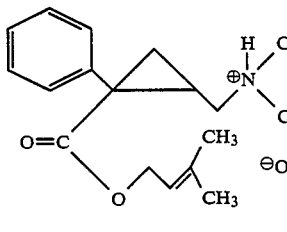

Empirical formula: $C_{22}H_{29}NO_6$.
Molecular weight: 403.6.

Crystals: clear beige.
Melting point: 114° C.
Plate chromatography:
support: silica gel 60 F 254 Merck
solvent: butanol/acetic acid/water 6/2/2
development: UV and iodine
Rf: 0.36

EXAMPLE 41

1-(4'-chlorophenyl) 1-ethoxycarbonyl 2-dimethylaminomethyl cyclopropane (Z) hydrochloride In a manner similar to that described in Examples 1a and 1b, but using the lactone of 1-p(chlorophenyl) 2-hydroxymethyl cyclopropane (Z) carboxylic acid and dimethylamine, there is obtained a product of the formula:

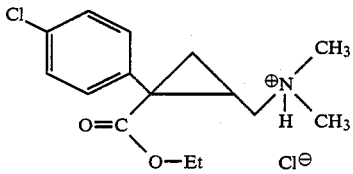

Empirical formula: $C_{15}H_{21}Cl_2NO_2$.
Molecular weight: 318.25.
Crystals: clear beige.
Melting point: 132° C.
Plate chromatography:
support: silica gel 60 F 254 Merck
solvent: chloroform/methanol/ammonia 84/14/2
development: UV and iodine
Rf: 0.7

EXAMPLE 42

Hydrochloride of 1-(α-naphthyl) 1-ethoxycarbonyl 2-dimethylamino methyl cyclopropane (Z)

In a manner similar to that described in Examples 1a and 1b, but using the lactone of α-naphthyl 2-hydroxymethyl cyclopropane carboxylic acid (Z) and dimethylamine, there is obtained a product of the formula:

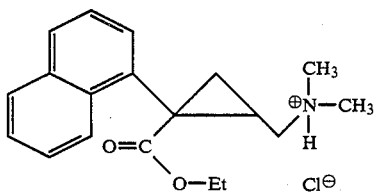

Empirical formula: $C_{19}H_{24}ClNO_2$.
Molecular weight: 333.86.
Crystals: white.
Melting point: 173° C.
Plate chromatography:
support: silica gel 60 F 254 Merck
solvent: butanol/acetic acid/water 6/2/2
development: UV and iodine
Rf: 0.34

EXAMPLE 43

Hydrochloride of 1-(4'-sulfamoyl phenyl) 1-methoxycarbonyl 2-dimethylaminomethyl cyclopropane (Z)

In a manner similar to that described in Example 1, but using 1-(4'-sulfamoyl phenyl) 2-oxo 3-oxa bicyclo(3:1:0)hexane, methyl alcohol and dimethylamine, there is obtained a product of the formula:

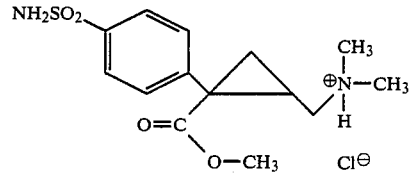

Empirical formula: $C_{14}H_{21}ClNO_4S$.
Molecular weight: 348.8.
Crystals: clear beige.
Melting point: 214° C.
Plate chromatography:
support: silica gel 60 F 254 Merck
solvent: chloroform/methanol/water 65/25/4
development: UV and iodine
Rf: 0.25

EXAMPLE 44

Maleate of 1-(m-chlorophenyl) 1-ethoxycarbonyl 2-dimethylaminomethyl cyclopropane (Z)

In a manner similar to that described in Example 1, but using the lactone of 1-(m-chlorophenyl) 2-hydroxymethyl cyclopropane carboxylic acid (Z) and dimethylamine, there is obtained a product of the formula:

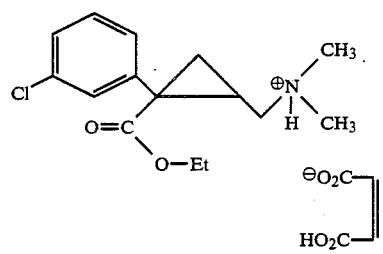

Empirical formula: $C_{19}H_{24}ClNO_6$.
Molecular weight: 397.8.
Crystals: white.
Melting point: 85° C.
Plate chromatography:
support: silica gel 60 F 254 Merck
solvent: butanol/acetic acid/water 6/2/2
development: UV and iodine
Rf: 0.42.

EXAMPLE 45

Hydrochloride of 1-(3,4 dichlorophenyl) 1-ethoxycarbonyl 2-dimethylaminomethyl cyclopropane (Z)

In a manner similar to that described in Example 1, but using 1-(3',4'-dichlorophenyl) 2-oxo 3-oxa bicyclo (3:1:0) hexane and dimethylamine, there is obtained a product of the formula:

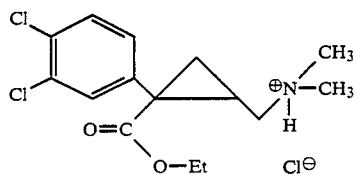

Empirical formula: $C_{15}H_{20}Cl_3NO_2$.
Molecular weight: 352.7.
Crystals: white.
Melting point: 148° C.
Plate chromatography:
support: silical gel 60 F 254 Merck
solvent: butanol/acetic acid/water 6/2/2
development: UV and iodine
Rf: 0.37

EXAMPLE 46

Maleate of 1-(p-aminophenyl) 1-methyloxycarbonyl 2-dimethylaminomethyl cyclopropane (Z)

In a manner similar to that described in Example 1, but using 1-(p-aminophenyl) 2-oxo 3-oxa bicyclo (3:1:0) hexane, methanol and dimethylamine, there is obtained a product of the formula:

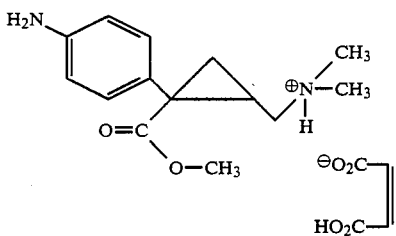

Empirical formula: $C_{18}H_{24}N_2O_6$.
Molecular weight: 364.4.
Crystals: white.
Melting point: 110° C.
Plate chromatography:
support: silica gel 60 F 254 Merck
solvent: chloroform/methanol/ammonia 80/18/2
development: UV and iodine
Rf: 0.66

EXAMPLE 47

Hydrochloride of 1-(p-nitrophenyl) 1-methoxycarbonyl 2-dimethylaminomethyl cyclopropane (Z)

In a manner similar to that described in Example 1, but using 1-(4'-nitrophenyl) 2-oxo 3-oxa bicyclo (3:1:0) hexans, methanol and dimethylamine, there is obtained a product of the formula:

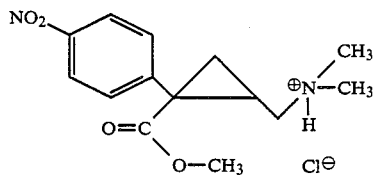

Empirical formula: $C_{14}H_{19}ClN_2O_4$.
Molecular weight: 314.8.
Crystals: white.

Melting point: 210° C.
Plate chromatography:
support: silica gel 60 F 254 Merck
solvent: chloroform/methanol/water 80/18/2
development: UV and iodine
Rf: 0.64

EXAMPLE 48

Hydrochloride of 1-(p-methoxy phenyl) 1-ethoxycarbonyl 2-dimethylaminomethyl cyclopropane (Z)

In a manner similar to that described in Example 1, but using 1-(p-methoxy phenyl) 2-oxo 3-oxa bicyclo (3:1:0) hexane and dimethylamine, there is obtained a product of the formula:

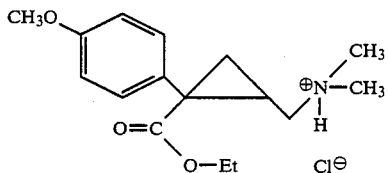

Empirical formula: $C_{16}H_{24}ClNO_3$.
Molecular weight: 313.8.
Crystals: white.
Melting point: 170° C.
Plate chromatography:
support: silica gel 60 F 254 Merck
solvent: butanol/acetic acid/water 6/2/2
development: UV and iodine
Rf: 0.49

EXAMPLE 49

Hydrochloride of 1-p-toluyl 1-(2'-propenyloxy carbonyl) 2-dimethylaminomethyl cyclopropane (Z)

In a manner similar to that described in Example 1, but using 1-p-toluyl 2-oxo 3-oxa bicyclo (3:1:0) hexane, allyl alcohol and dimethylamine, there is obtained a product of the formula:

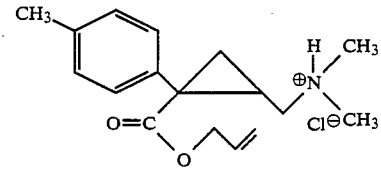

Empirical formula: $C_{17}H_{24}ClNO_2$.
Molecular weight: 309.8.
Crystals: white.
Melting point: 154° C.
Plate chromatography:
support: silica gel 60 F 254 Merck
solvent: chloroform/methanol 85/15
development: UV and iodine
Rf: 0.41

EXAMPLE 50

Hydrochloride of 1-(3',4'-dichlorophenyl) 1-(2'-propenyloxy carbonyl) 2-dimethylaminomethyl cyclopropane (Z)

In a manner similar to that described in Example 1, but using 1-(3',4'-dichlorophenyl) 2-oxo 3-oxa bicyclo (3:1:0) hexane, allyl alcohol and dimethylamine, there is obtained a product of the formula:

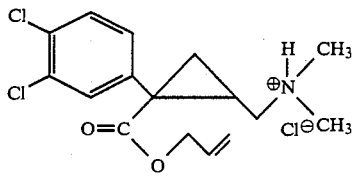

Empirical formula: $C_{16}H_{20}Cl_3NO_2$
Molecular weight: 364.7.
Crystals: white.
Melting point: 160° C.
Plate chromatography:
support: silica gel 60 F 254 Merck
solvent: chloroform/methanol 15/85
development: UV and iodine
Rf: 0.45

EXAMPLE 51

Hydrochloride of 1-parafluorophenyl 1-ethoxycarbonyl 2-dimethylaminomethyl cyclopropane (Z)

In a manner similar to that described in Example 1, but using 1-p-fluorophenyl 2-oxo 3-oxa bicyclo (3:1:0) hexane and dimethylamine, there is obtained a product of the formula:

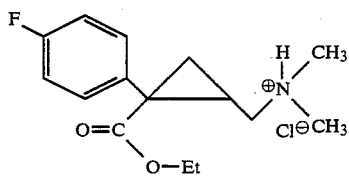

Empirical formula: $C_{15}H_{21}FClNO_2$.
Molecular weight: 301.7.
Crystals: white.
Melting point: 165° C.
Plate chromatography:
support: silica gel 60 F 254 Merck
solvent: butanol/acetic acid/water
development: UV and iodine
Rf: 0.36

EXAMPLE 52

Hydrochloride of 1-(p-chlorophenyl) 1-ethoxycarbonyl 2-aminomethyl cyclopropane (Z)

In a manner similar to that described in Example 1, but using 1-(p-chlorophenyl) 2-oxo 3-oxa bicyclo (3:1:0) hexane and ammonia, there is obtained a product of the formula:

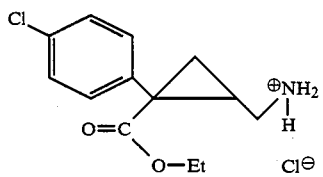

EXAMPLE 53

Hydrochloride of 1-(p-hydroxyphenyl) 1-ethoxycarbonyl 2-dimethylaminomethyl cyclopropane (Z)

In a manner similar to that described in Example 1, but using 1-(p-hydroxyphenyl) 2-oxo 3-oxa bicyclo (3:1:0) hexane and dimethylamine, there is obtained a product of the formula:

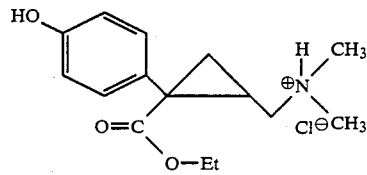

EXAMPLE 54

Hydrochloride of 1-(3',4',5'-trimethoxyphenyl) 1-ethoxycarbonyl 2-dimethylaminomethyl cyclopropane (Z)

In a manner similar to that described in Example 1, but using 1-(3',4',5'-trimethoxyphenyl) 2-oxo 3-oxa bicyclo (3:1:0) hexane and dimethylamine, there is obtained a product of the formula:

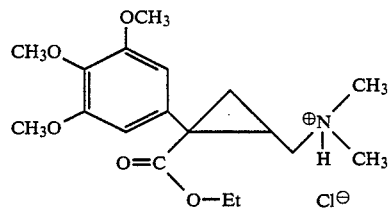

EXAMPLE 55

Hydrochloride of 1-orthobromophenyl 1-ethoxycarbonyl 2-dimethylaminomethyl cyclopropane (Z)

In a manner similar to that described in Example 1, but using 1-orthobromophenyl 2-oxo 3-oxa bicyclo (3:1:0) hexane and dimethylamine, the product of formula

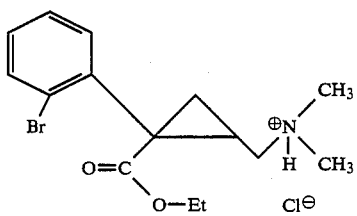

is obtained.

PHARMACOLOGICAL PROPERTIES (1) Toxicity Study

The most interesting compounds of the present invention were subjected to toxicity studies.

The $ED_{50}$ was determined orally and intraperitoneally and calculated by the method of MILLER and TAINTER (Proc. Soc. Exper. Biol. Chem. 1944, 57, 261).

The results are set forth in Table I below.

TABLE I

| PRODUCTS | $ED_{50}$ per os mg/kg | intra- perito- neally | Writhing Syndrome PBQ-$ED_{50}$ mg/kg (P.O.) | Hot Plate 50 mg/kg SC reaction time (seconds) |
|---|---|---|---|---|
| Example 30 | 1000 | 110 | 80 | 20 |
| Example 36 | 400 | 130 | 17 | 40 |
| Example 37 | 1000 | 130 | 92 | 30 |
| Example 41 | 400 | 120 | 19 | 39 |
| Example 44 | 760 | 170 | 30 | 28 |
| Example 45 | 550 | 170 | 60 | 26 |
| Example 46 | 420 | 100 | 34 | 25 |
| Example 47 | 1000 | 250 | 21 | 20 |
| Example 48 | 420 | 110 | 95 | 29 |
| Dextro- propoxyphene | | | 30 | 30 |

(2) Analgesic Activity (a) Writhing Syndrome (P.B.Q.)

After I.P. administration of p-benzoquinone to mice, the products were tested by the method of R. OKUN, S. C. LIDDON and L. LASAGNA, J. Pharmacol. Exptl. Therap., 1963, 139, 107. The results are expressed in $ED_{50}$ in Table 1.

(b) Hot Plate

The products were tested subcutaneously in mice (50 mg/kg) by the method of N. B. EDDY and D. LEIMBACH, J. Pharm. Exptl. Therap., 1953, 107, 385. The results are set forth in Table 1.

(3) Therapeutic Applications

On basis of their pharmacological properties and their low toxicity, these compounds can be used in therapy in the treatment of various pains, most especially the compounds of Examples 36, 41, 44, 46 and 47.

These compounds and their addition salts with therapeutically compatible acids can be used as drugs, for instance, in the form of adapted pharmaceutical preparations which facilitate bioavailability.

These preparations may be in solid form, for instance tablets, pills, capsules, etc., or in liquid form, for instance solutions, suspensions, or emulsions.

The pharmacological preparations in a form suitable for injection are subjected to conventional pharmaceutical operations such as sterilization and/or may contain adjuvants, for instance preservatives, stabilizers, wetting or emulsifying agents, buffer compounds, etc.

The doses in which the active compounds and their addition salts with therapeutically compatible acids can be administered may vary in wide proportions depending on the condition of the patient. A daily dose of from about 0.1 mg to 1 mg/kg of body weight is, however, preferred.

The pharmaceutical compositions of the invention can be used in human or veterinary medicine, for instance in the treatment of painful phenomena, particularly in cancerology, traumatology, rheumatology, neurology and surgery.

Other active principles can be associated with the compounds of general formula I of the invention in order to supplement or reinforce their therapeutic action within a given pharmaceutical composition.

EXAMPLES OF PHARMACEUTICAL PREPARATIONS

| A/ Tablets of prolonged effect | |
|---|---|
| 1-(4'-chlorophenyl) 1-ethoxycarbonyl 2-dimethylaminomethyl cyclopropane (Z) hydrochloride | 50 mg |
| Retard excipient Q.S.P. | 1 tablet |
| B/ Suppository | |
| 1-(4'-chlorophenyl) 1-ethoxycarbonyl 2-dimethylaminomethyl cyclopropane (Z) hydrochloride | 25 mg |
| Paracetamol | 300 mg |
| Excipient Q.S.P. | 1 adult suppository |

Of course, the present invention is not limited to the particular examples which have been given solely by way of illustration, but it is entirely possible to think of a number of variants and modifications thereof without thereby going beyond the scope of the invention.

We claim:

1. A 1-phenyl-1-lower-alkoxy carbonyl 2-aminomethyl cyclopropane (Z), wherein the 1-phenyl radical is substituted by hydroxy, methoxy, halo, amino, or nitro, and wherein aminomethyl is primary aminomethyl, monoloweralkylaminomethyl, or diloweralkylaminomethyl, or a pharmaceutically-acceptable acid addition salt thereof.

2. Compound of claim 1 wherein the compound is a 2-dimethylaminomethyl compound.

3. A compound of claim 1 which is 1-(4'-chlorophenyl) 1-ethoxycarbonyl 2-dimethylaminomethyl cyclopropane (Z) hydrochloride.

4. A compound of claim 1 which is the maleate of 1-(p-amino-phenyl) 1-methoxycarbonyl 2-dimethylaminomethyl cyclopropane (Z).

5. A compound of claim 1 which is 1-(4'-chlorophenyl) 1-ethoxycarbonyl 2-dimethylaminomethyl cyclopropane (Z) pharmaceutically-acceptable acid addition salt.

6. A compound of claim 1 which is a pharmaceutically-acceptable acid addition salt of 1-(p-aminophenyl) 1-methyloxycarbonyl 2-dimethylaminomethyl cyclopropane (Z).

7. A compound of claim 1 wherein the 1-phenyl is chloro substituted.

8. A compound of claim 1 wherein the 1-phenyl is para-chloro substituted.

* * * * *